(12) United States Patent
Koss et al.

(10) Patent No.: US 9,228,679 B2
(45) Date of Patent: Jan. 5, 2016

(54) HOLDING A FLEXIBLE ELONGATE OBJECT

(71) Applicant: Covidien LP, Mansfield, MA (US)

(72) Inventors: Andrew Koss, Middleboro, MA (US); Steven Cote, Mendon, MA (US)

(73) Assignee: Covidien LP, Mansfield, MA (US)

( * ) Notice: Subject to any disclaimer, the term of this patent is extended or adjusted under 35 U.S.C. 154(b) by 46 days.

(21) Appl. No.: 14/103,939

(22) Filed: Dec. 12, 2013

(65) Prior Publication Data

US 2015/0167865 A1    Jun. 18, 2015

(51) Int. Cl.
*F16L 3/08* (2006.01)
*F16L 3/137* (2006.01)
*B65H 75/00* (2006.01)

(52) U.S. Cl.
CPC ............... *F16L 3/137* (2013.01); *B65H 75/00* (2013.01)

(58) Field of Classification Search
CPC ............ F16L 3/137; F16L 3/00; F16L 3/1218
USPC .......................................................... 248/70
See application file for complete search history.

(56) References Cited

U.S. PATENT DOCUMENTS

| | | | | |
|---|---|---|---|---|
| 504,307 A * | 8/1893 | Roberts | .......................... | 294/154 |
| 1,175,024 A * | 3/1916 | Thorson | .......................... | 294/154 |
| 3,012,809 A * | 12/1961 | Tremaine | ..................... | 294/31.2 |
| 4,128,220 A | 12/1978 | McNeel | | |
| 4,182,005 A | 1/1980 | Harrington | | |
| 4,501,354 A | 2/1985 | Hoffman | | |
| 4,842,158 A * | 6/1989 | Reyes, Jr. | ...................... | 222/470 |
| 5,042,114 A | 8/1991 | Parrish | | |
| 5,096,248 A * | 3/1992 | Ryan | .............................. | 294/156 |
| 5,199,135 A | 4/1993 | Gold | | |
| 5,348,362 A * | 9/1994 | Rolls | .............................. | 294/151 |
| 5,715,578 A | 2/1998 | Knudson | | |
| 6,499,199 B2 | 12/2002 | Frazier | | |
| 6,729,665 B1 * | 5/2004 | Posey et al. | ................... | 294/31.2 |
| 6,976,719 B2 | 12/2005 | Agayof et al. | | |
| 7,540,069 B2 | 6/2009 | Okamoto | | |
| 7,976,088 B1 * | 7/2011 | Diciolla | ......................... | 294/154 |
| 8,042,232 B2 | 10/2011 | Mask et al. | | |
| 8,191,207 B1 | 6/2012 | Holscher | | |
| 8,246,095 B2 | 8/2012 | Radle et al. | | |
| 2003/0088948 A1 | 5/2003 | Cook | | |
| 2005/0029419 A1* | 2/2005 | Ware et al. | .................. | 248/218.4 |
| 2006/0012199 A1 | 1/2006 | Slank | | |
| 2007/0152460 A1 | 7/2007 | Bauer | | |
| 2009/0090819 A1* | 4/2009 | Crook | ............................. | 248/49 |
| 2010/0083469 A1 | 4/2010 | Welker | | |
| 2012/0277682 A1 | 11/2012 | Corato et al. | | |

* cited by examiner

*Primary Examiner* — Mark Wendell
(74) *Attorney, Agent, or Firm* — John Paul Mello, Esq.

(57) ABSTRACT

A holder which has a loop portion securable around a flexible elongate in a folded configuration. A spine portion is coupled to the loop portion. At least one movable portion is adjustable between a first position, in which the at least one movable portion forms at least a portion of a handle in a substantially coplanar orientation relative to the spine portion, and a second position, in which the at least one movable portion forms at least one hook in a substantially transverse orientation relative to the spine portion. The at least one hook is positionable on a structure to support the loop portion in a hanging position on the structure.

15 Claims, 22 Drawing Sheets

HOLDING A FLEXIBLE ELONGATE OBJECT

BACKGROUND

Flexible elongate objects are common across many industries, including the healthcare industry. Such objects can include, for example, flexible tubes, power cords, communication wires, straps, and cables. When in use, these objects can become tangled, making them cumbersome to move from place to place as needed. In a hospital setting, such tangled objects can pose a hazard in the vicinity of a patient's bed. Moreover, unintended tangling and bending of a flexible elongate object could adversely affect the operation of the flexible elongate object. This could include, for example, a fluid delivery tube being kinked to restrict fluid flow and/or a power cord becoming unplugged.

SUMMARY

A holder for holding a flexible elongate object includes a loop portion, a spine portion, and at least one movable portion. The loop portion is securable around the flexible elongate object with the flexible elongate object in a folded configuration. The spine portion is coupled to the loop portion. The at least one movable portion is adjustable between a first position, in which the at least one movable portion forms at least a portion of a handle in a substantially coplanar orientation relative to the spine portion, and a second position, in which the at least one movable portion forms at least one hook in a substantially transverse orientation relative to the spine portion. The at least one hook is positionable on a structure to support the loop portion in a hanging position on the structure.

In some embodiments, the loop portion defines a center axis when secured around the folded configuration of the flexible elongate object. The center axis is parallel to portions of the folded flexible elongate object extending through the loop portion, and the center axis of the loop portion is parallel to the handle when the at least one movable portion is in the substantially coplanar orientation relative to the spine portion.

In certain embodiments, in the second position, the at least one movable portion and the center axis are nonparallel to one another. For example, in the second position, the at least one movable portion can be generally perpendicular to the center axis.

In some embodiments, the holder includes a lock releasably securable to the at least one movable portion in the second position.

In certain embodiments, the spine portion defines a channel and the lock includes a tab receivable in the channel when the at least one movable portion is in the second position.

In certain embodiments, the loop portion comprises a first loop member and a second loop member, with the first and second loop members axially aligned with one another along the center axis.

In some embodiments, the first and second loop members are coupled to the spine portion, at opposite ends of the spine portion.

In certain embodiments, the at least one movable portion is connected to the spine portion generally between the first and second loop members.

In some embodiments, the at least one hook, formed by the at least one movable portion in the second position, is adjustable between a first hanging position and a second hanging position, and the structure is positionable between the at least one movable portion and the spine portion in each of the first and second hanging positions.

In certain embodiments, in the first hanging position, the movable portion is resiliently biased toward the first position in which the at least one movable portion is substantially coplanar with the spine portion.

In some embodiments, the holder further includes a lock releasably securable to the at least one movable portion in the second hanging position.

In some embodiments, the loop portion includes first and second end sections releasably attachable to one another to secure the loop portion around the flexible elongate object in the folded configuration.

In some embodiments, the loop portion includes a releasably attachable clasp.

Embodiments can include one or more of the following advantages.

In some embodiments, a flexible elongate object is secured in a folded configuration and secured in place by the loop portion such that the flexible elongate object may be transported while secured in the folded configuration. This can reduce, for example, damage to the flexible elongate object during transport and, additionally or alternatively, increase the likelihood that the object is in a ready-to-use configuration upon completion of transport.

In certain embodiments, the at least one movable portion is movable to support a flexible elongate object on structures of varying thicknesses. Operability of the holder with a broad class of support structures improves versatility and facilitates supporting a flexible elongate object in a folded configuration in many settings, such as, for example, many medical facilities and/or in a variety of home settings. For example, the holder may be secured to structures such as bed sheets, bed frames, footboards, medical cart frames, and the like.

In some embodiments, the holder transitions from a first position in which the at least one movable portion forms a portion of a convenient handle for transporting the holder to a second position in which the at least one movable portion forms a portion of a hook for supporting the flexible elongate object in a folded configuration on a structure. Thus, for example, the movement of the at least one movable portion between the first position and the second position may facilitate the transport and storage of a flexible elongate object using the same device. This can reduce the amount of handling required of the elongate flexible object which can, for example, reduce the likelihood that the elongate flexible object will become entangled.

In certain embodiments, the holder includes a lock that secures at least one movable portion in place as a hook to define a space for receiving a structure. The space remains locked in a fixed position with respect to the holder so that a user can quickly and assuredly secure the holder to the structure.

Other aspects, embodiments, features, and advantages will be apparent in view of the following description and drawings, and from the claims.

BRIEF DESCRIPTION OF THE DRAWINGS

Corresponding reference characters indicate corresponding parts throughout the drawings.

DETAILED DESCRIPTION OF THE DRAWINGS

Figure 1:
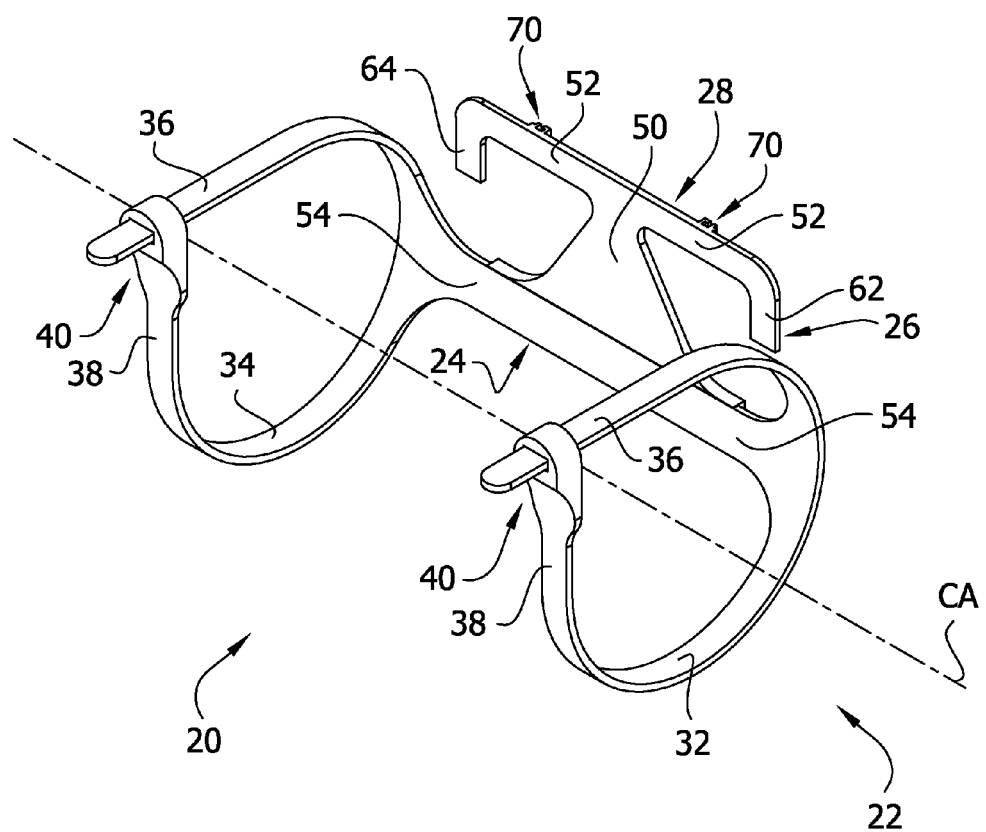
FIG. 1 is a front perspective view of a holder, shown with a movable portion in a first position.
Figure 2:
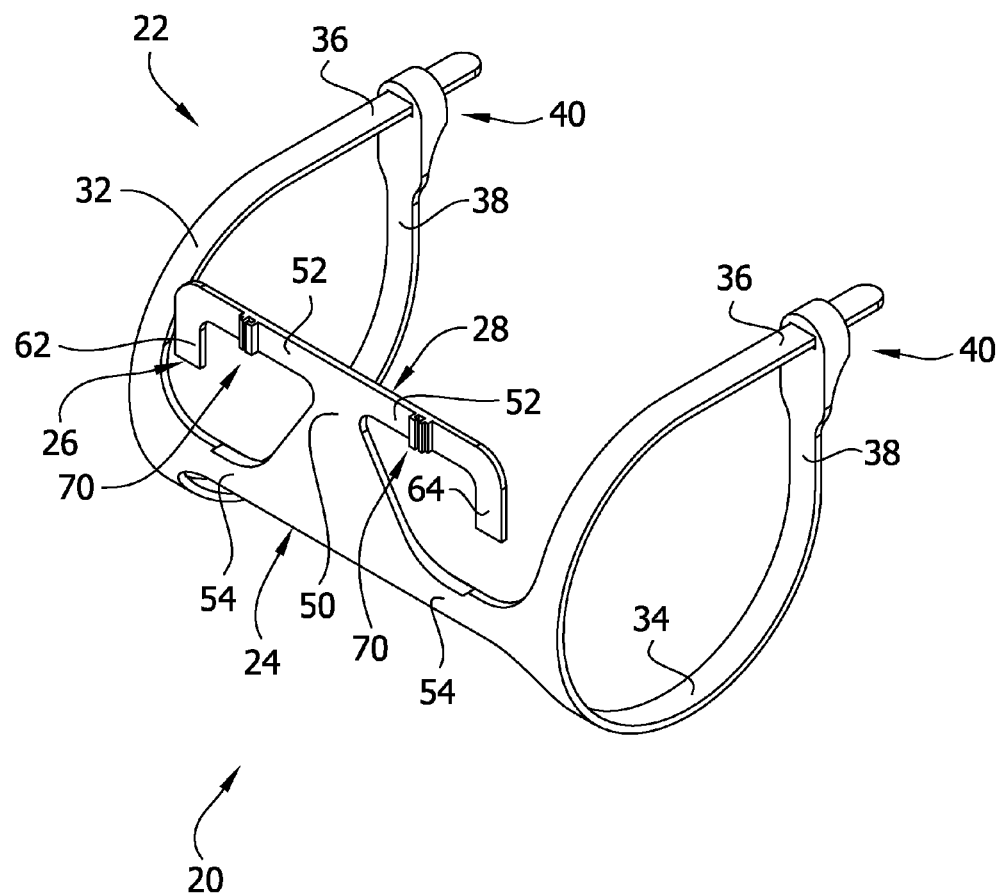
FIG. 2 is a rear perspective view of the holder of FIG. 1, shown with the movable portion in the first position.
Figure 3:
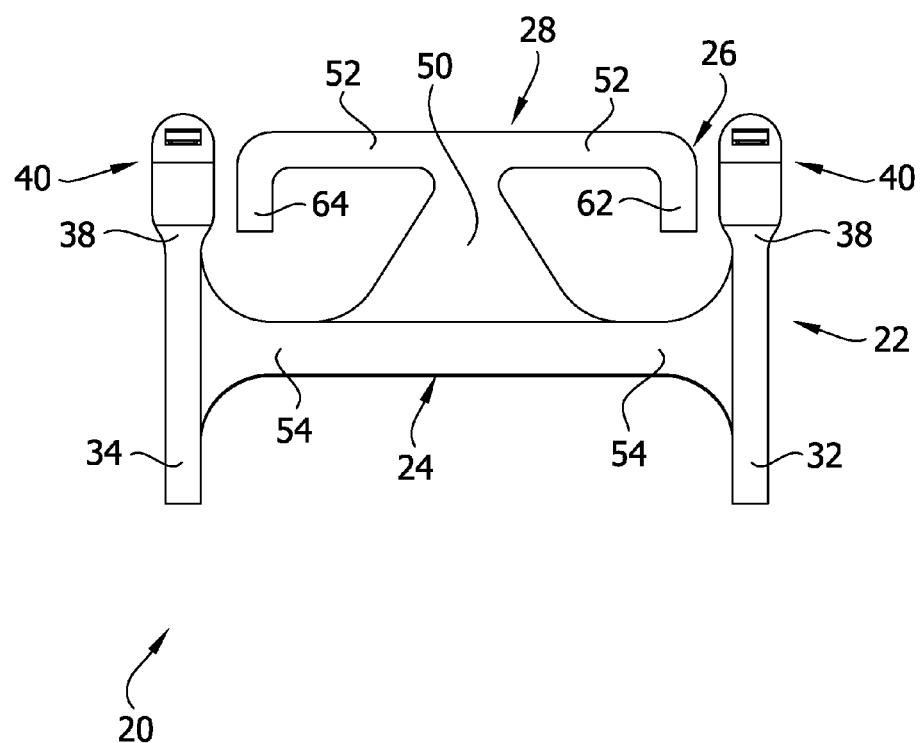
FIG. 3 is a front elevation view of the holder of FIG. 1, shown with the movable portion in the first position.
Figure 4:
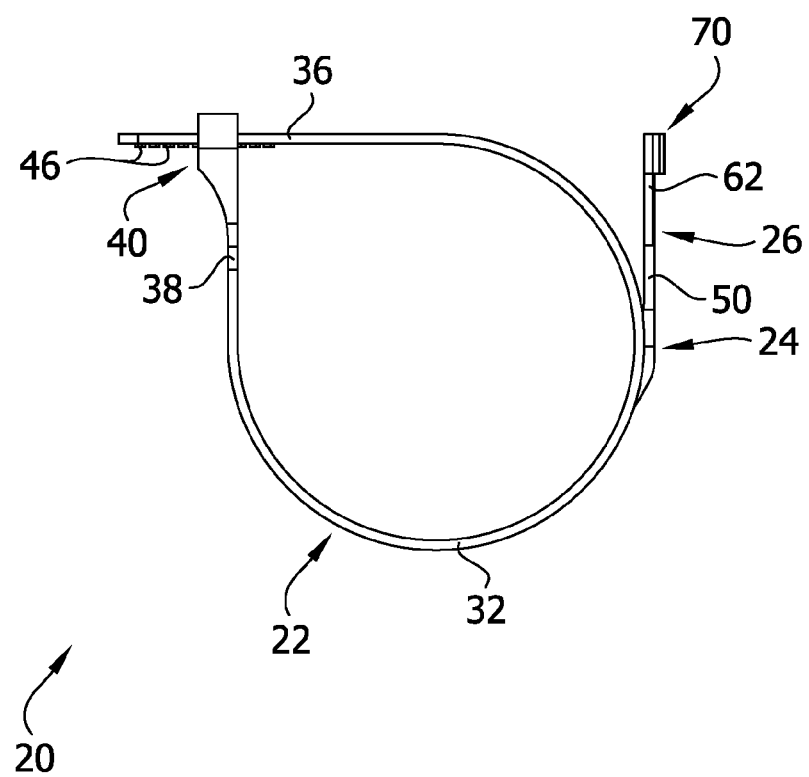
FIG. 4 is a right side elevation view of the holder of FIG. 1, shown with the movable portion in the first position, the left side elevation view being a mirror image thereof.
Figure 5:
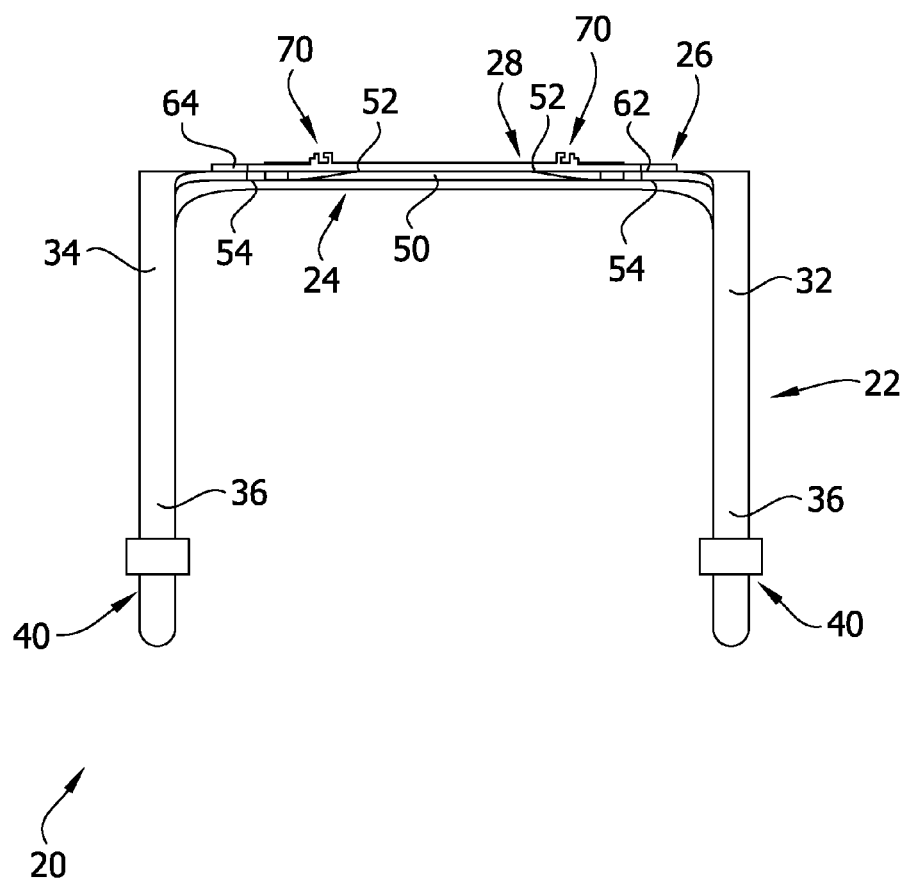
FIG. 5 is a top plan view of the holder of FIG. 1, shown with the movable portion in the first position.
Figure 6:
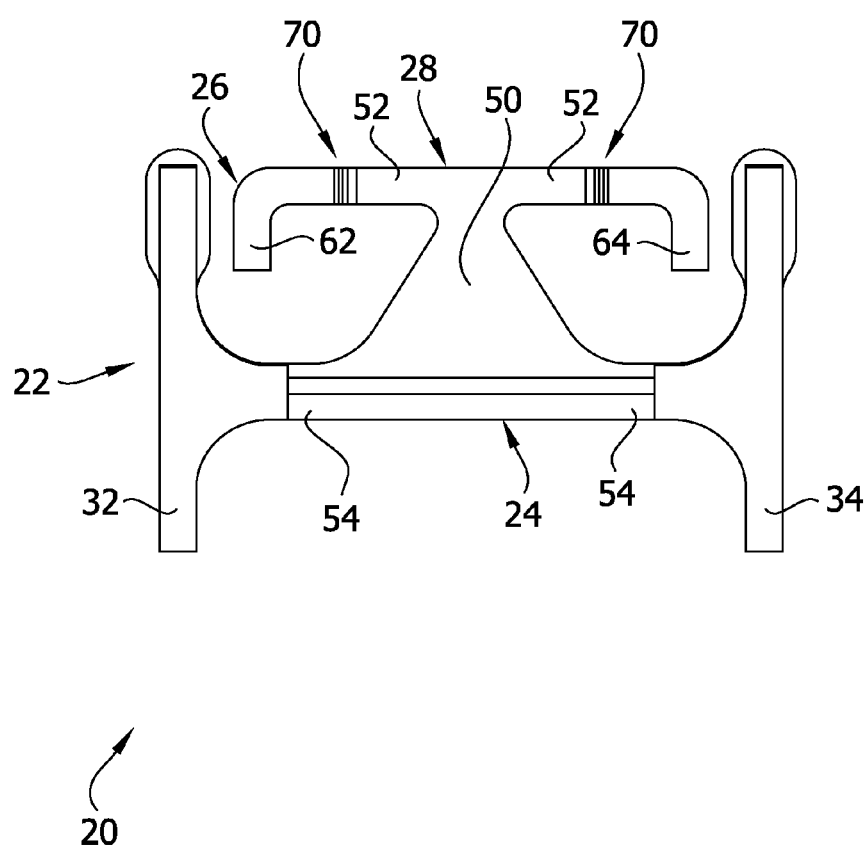
FIG. 6 is a rear elevation view of the holder of FIG. 1, shown with the movable portion in the first position.
Figure 7:
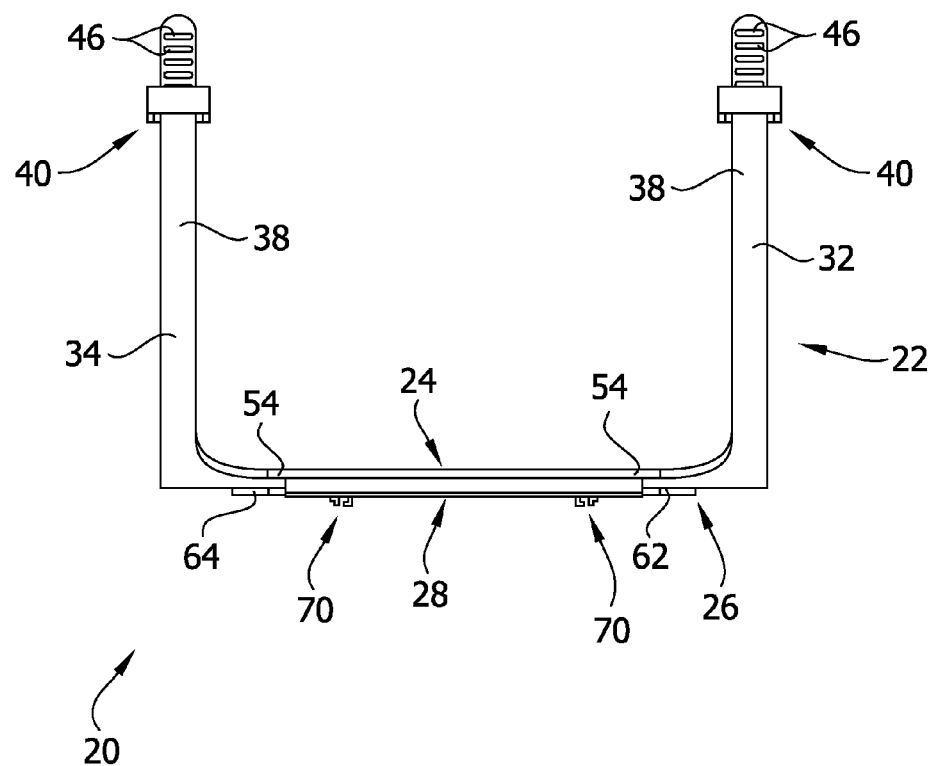
FIG. 7 is a bottom plan view of the holder of FIG. 1, shown with the movable portion in the first position.
Figure 8:
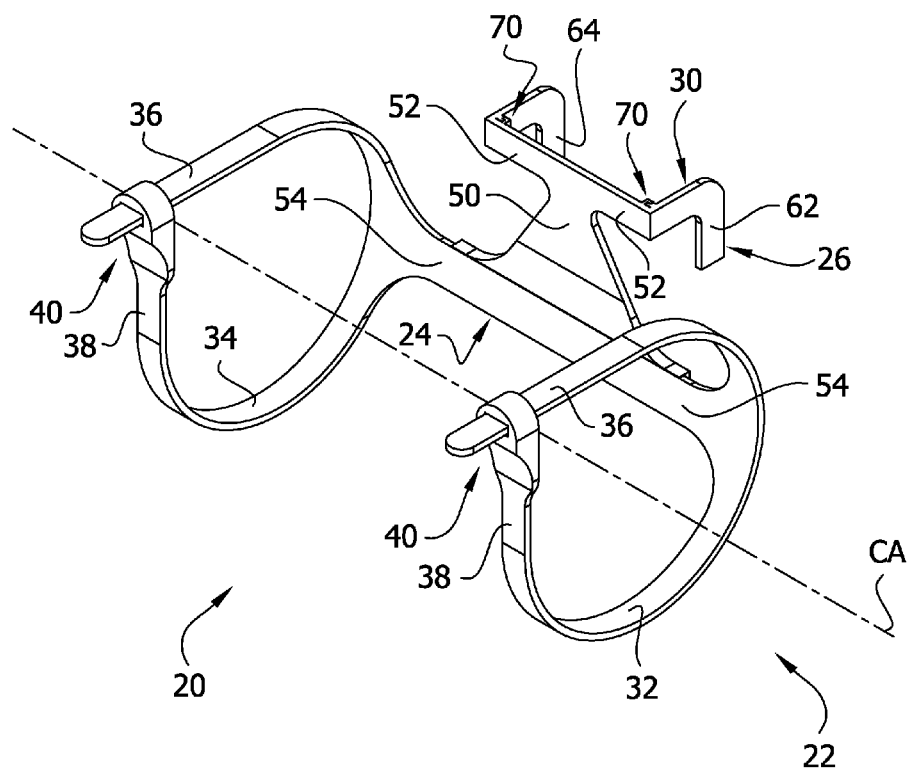
FIG. 8 is a front perspective view of the holder of FIG. 1, shown with the movable portion in a second position.
Figure 9:
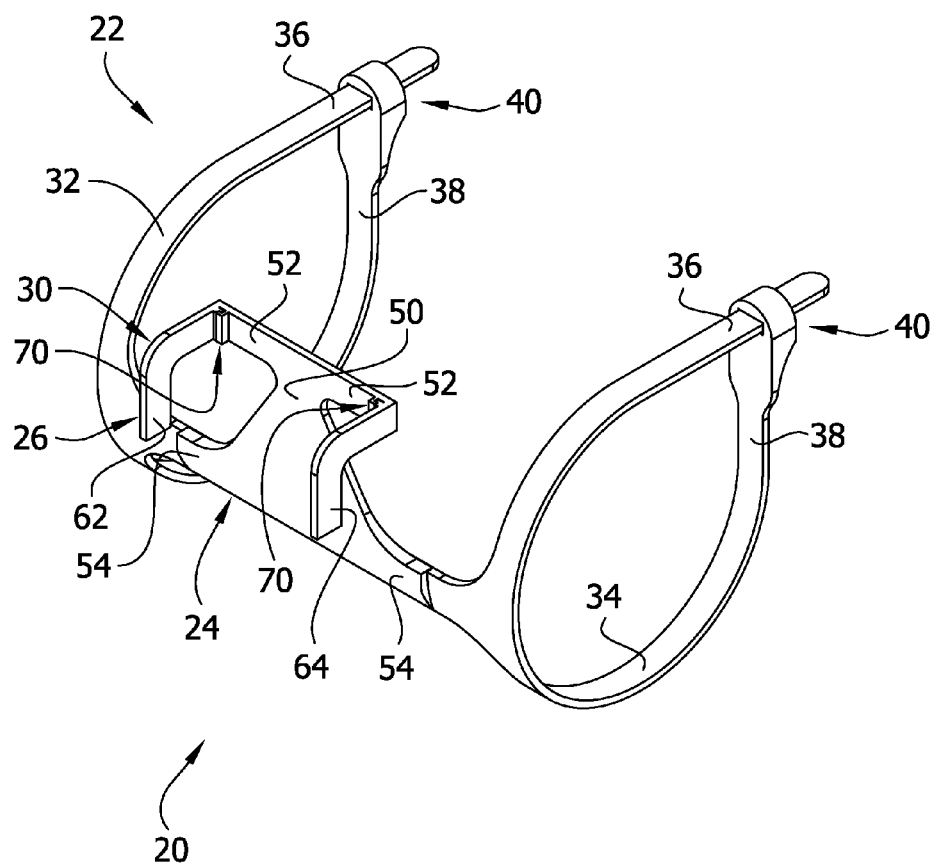
FIG. 9 is a rear perspective view of the holder of FIG. 1, shown with the movable portion in the second position.
Figure 10:
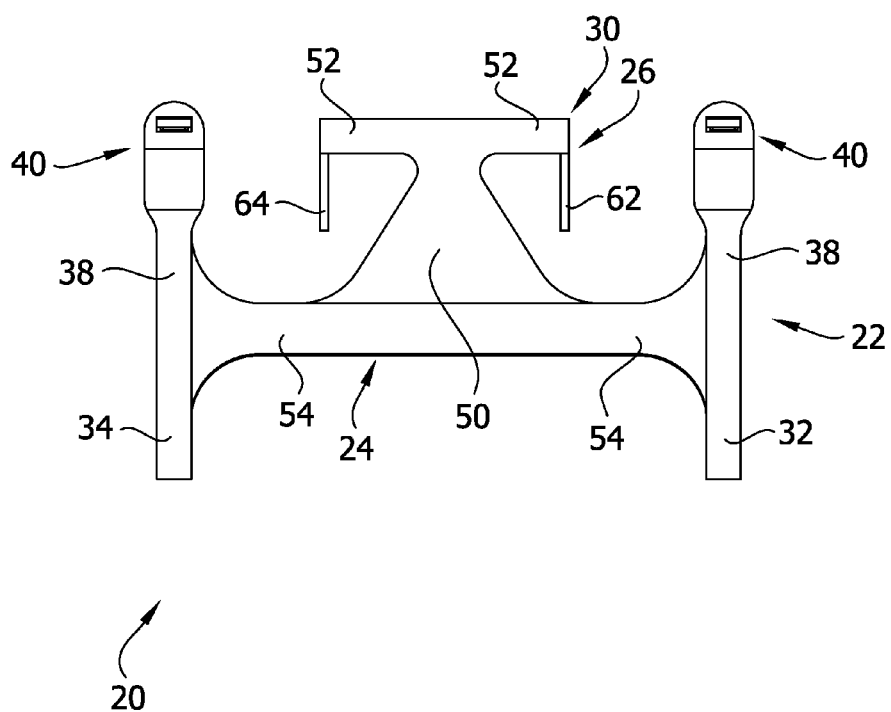
FIG. 10 is a front elevation view of the holder of FIG. 1, shown with the movable portion in the second position.
Figure 11:
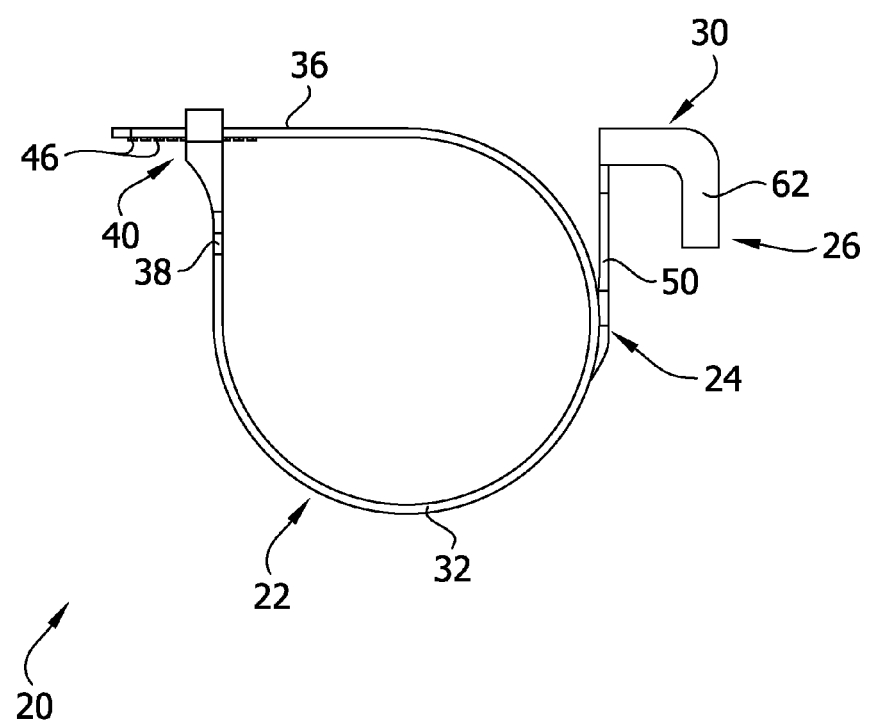
FIG. 11 is a right side elevation view of the holder of FIG. 1, shown with the movable portion in the second position, the left side elevation view being a mirror image thereof.
Figure 12:
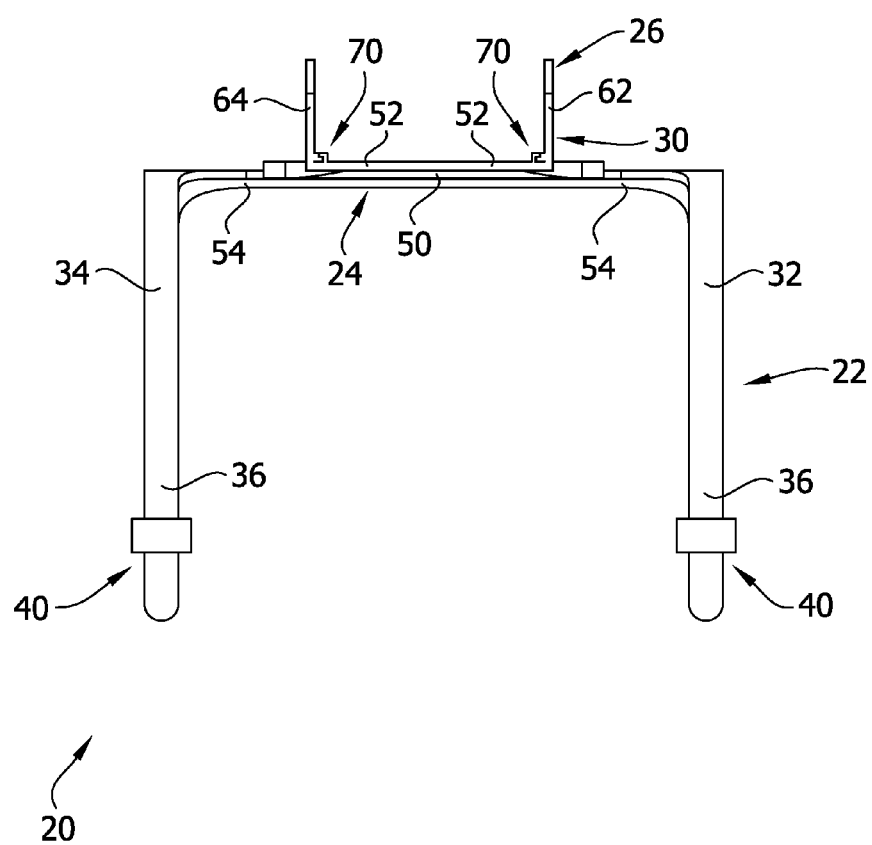
FIG. 12 is a top plan view of the holder of FIG. 1, shown with the movable portion in the second position.
Figure 13:
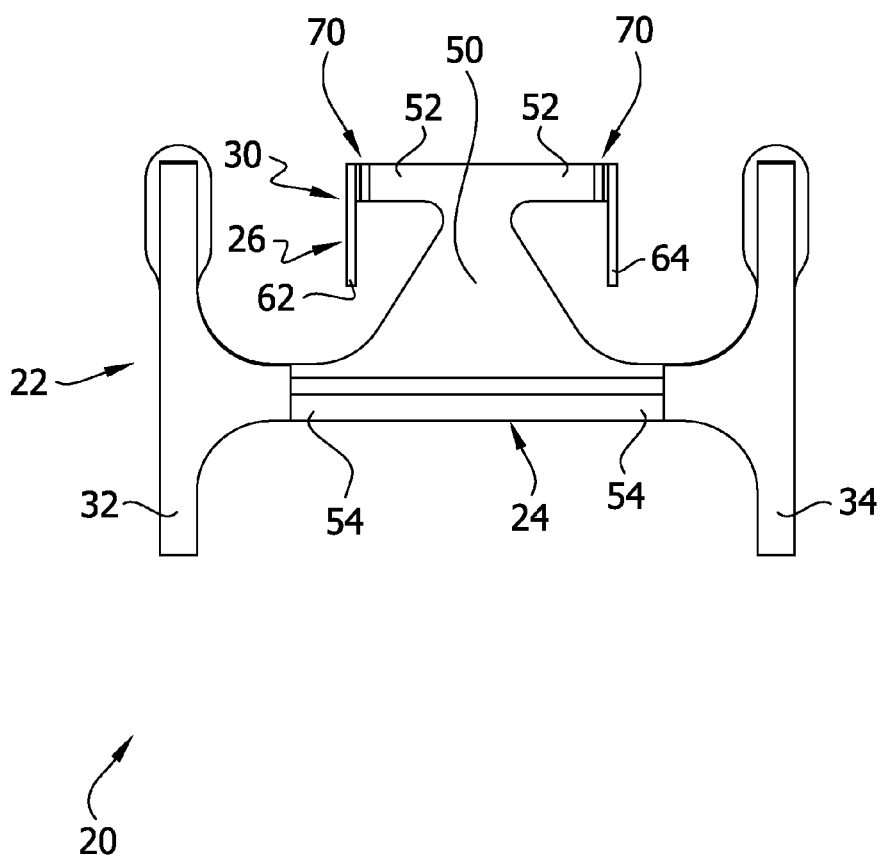
FIG. 13 is a rear elevation view of the holder of FIG. 1, shown with the movable portion in the second position.
Figure 14:
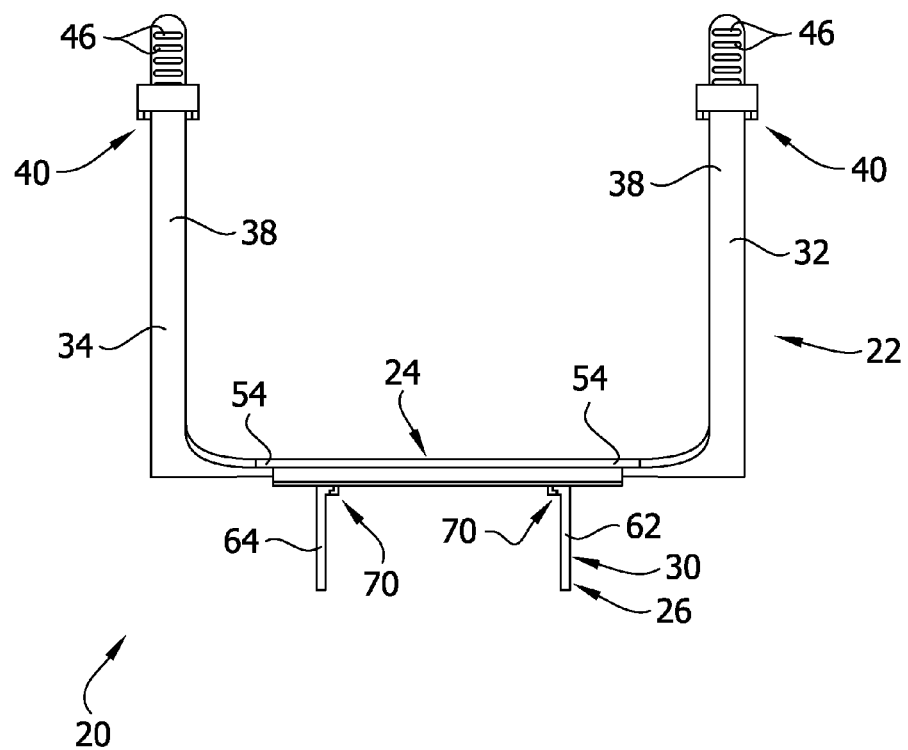
FIG. 14 is a bottom plan view of the holder of FIG. 1, shown with the movable portion in the second position.

Referring to FIGS. 1-14, a holder 20 includes a loop portion 22, a spine portion 24, and a movable portion 26. The loop portion 22 and the movable portion 26 are each coupled to the spine portion 24. The movable portion 26 is adjustable between a first position (FIGS. 1-7) and a second position (FIGS. 8-14). When in the first position, the movable portion 26 forms at least a portion of a handle 28 that can be used for carrying the holder 20 and any flexible elongate object secured by the holder 20. In the second position, the movable portion 26 forms a hook 30 in a substantially transverse orientation (e.g., forming an angle of between about 80° and about 110°) relative to the spine portion 24. The hook 30 can be engaged with, for example, a footboard and/or a frame of a bed to mount the holder 20 and a flexible elongate object on the bed, as will be described in further detail below. The adjustability of the holder 20 from the first position to the second position can facilitate, for example, the handling and storage of a flexible elongate object in a manner that will reduce the likelihood of hazards (e.g., tripping hazards) associated with handling and storing the flexible elongate object in the vicinity of a patient's bed, where space is often limited.

The loop portion 22 includes a first loop member 32 and a second loop member 34. The first loop member 32 and the second loop member 34 are axially aligned with one another such that the loop portion 22 defines a center axis CA when the first loop member 32 and the second loop member 34 are secured around a folded configuration of a flexible elongate object. The center axis CA is generally parallel to portions of a folded configuration of a flexible elongate object secured by the first loop member 32 and the second loop member 34. This orientation can facilitate holding the flexible elongate object in place while the first loop member 32 and the second loop member 34 are unsecured (e.g., as the flexible elongate object is manipulated into the folded configuration).

The first loop member 32 and second loop member 34 are coupled to the spine portion 24 at opposite ends of the spine portion 24. The movable portion 26 is connected to the spine portion 24, generally between the first loop member 32 and the second loop member 34. Although two loop members 32 and 34 are shown, it should be appreciated that one loop member or more than two loop members may also be used. Additionally or alternatively, the first and second loop members 32, 34 may be connected at locations other than the spine portion 24.

The loop members 32, 34 each include first and second end sections 36, 38 releasably attachable to one another to secure the respective loop member 32, 34 around a flexible elongate object in a folded configuration of the object. It should be understood that a folded configuration of a flexible elongate object may include configurations such as, for example, looped, bunched, or other wrapped configurations, in addition to sheepshank-type configurations in which the object is folded back and forth upon itself.

The first and section end sections 36, 38 may include, for example, flexible straps of material with elasticity sufficient to flex upon engagement with a flexible elongate object. Such flexing can, for example, facilitate holding a flexible elongate object in place on the holder 20 while reducing the likelihood of abrasion, kinking, and/or other types of damage to the flexible elongate object.

Figure 15:
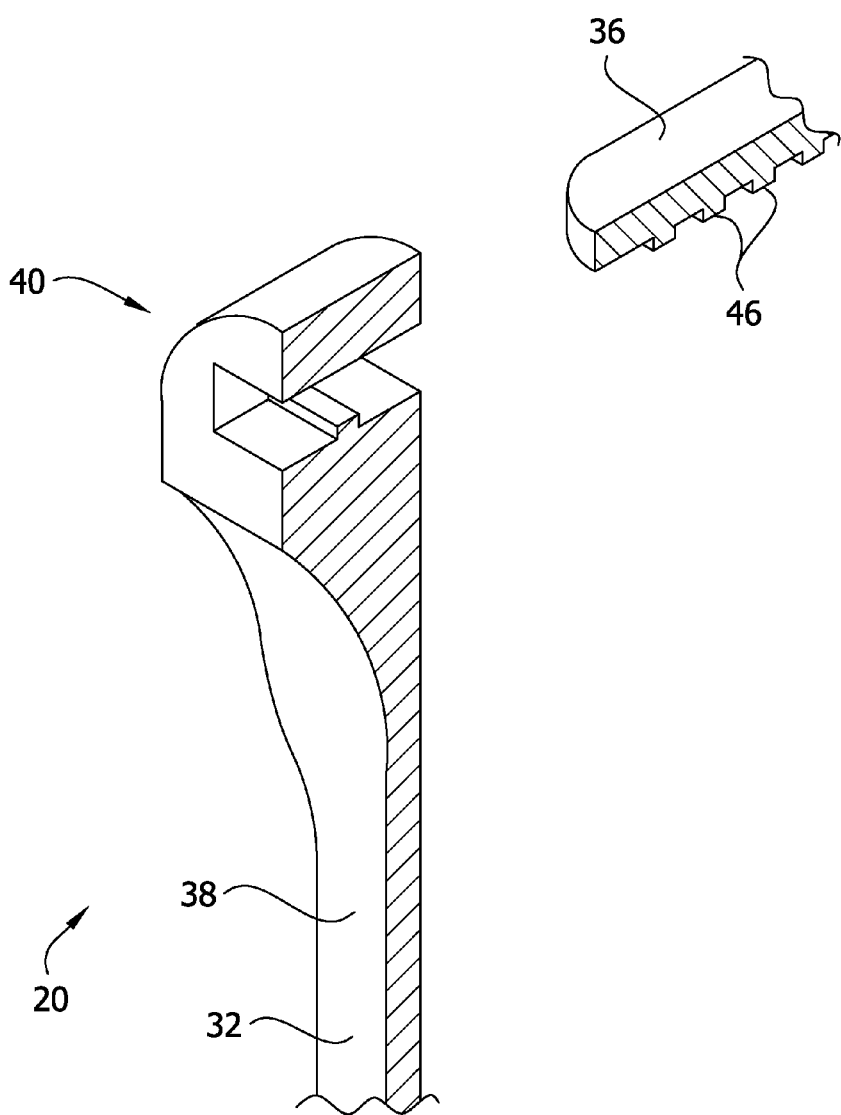
FIG. 15 is an enlarged, fragmentary cross-sectional perspective view of a loop member of the holder of FIG. 1, shown with a loop portion in an open position.
Figure 16:
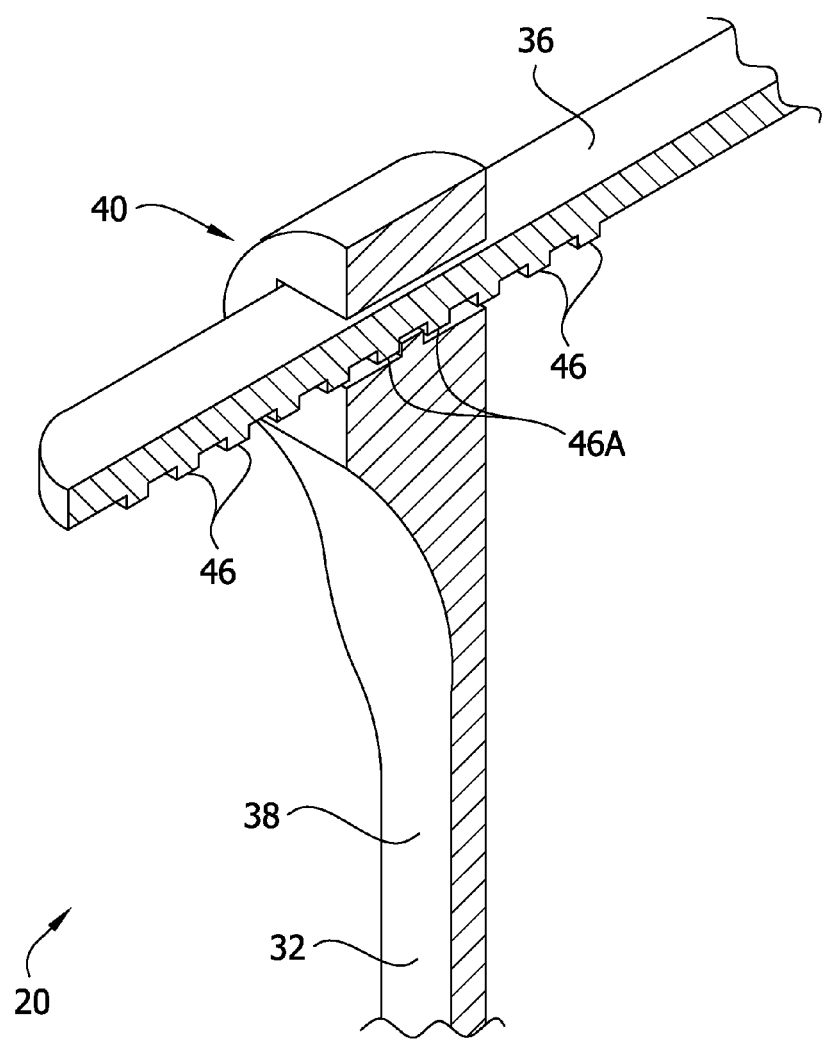
FIG. 16 is an enlarged, fragmentary cross-sectional perspective view of the loop member of FIG. 15, shown with the loop portion in a closed position.

Each of the loop members 32, 34 also includes a releasably attachable clasp 40. The clasp 40 may be used to selectively configure first and second loop members 32, 34 in an open position (FIG. 15) and a closed position (FIG. 16). In the open position shown in FIG. 15, the first and second end sections 36, 38 of the first loop member 32 are disconnected from one another. In the closed position shown in FIG. 16, the end sections 36, 38 are connected to one another. Only the first loop member 32 is shown in FIGS. 15 and 16, but it should be appreciated that the following description also applies to the second loop member 34.

The clasp 40 defines an opening 42 sized and shaped to receive the first end section 36 through the opening 42. A step 44 in the opening 42 is engageable with teeth 46 formed on the underside of the first section 36. As the first section 36 is pushed through the opening 42, the teeth 46 sequentially engage the step 44. If sufficient force is applied, at least one of the step 44 and tooth 46 engaging the step will deform to allow the tooth 46 to pass over the step 44. The teeth 46A prevent the first section 36 from being withdrawn from the opening 42 until a sufficient force is applied along an axis passing through the opening 42. Any of several positions may be selected with the step 44 located between two adjacent teeth 46 such that the overall circumference of the first loop member 32 can be adjusted according to a desired amount of tension to retain a flexible elongate member secured within the loop member 32.

Figure 17:
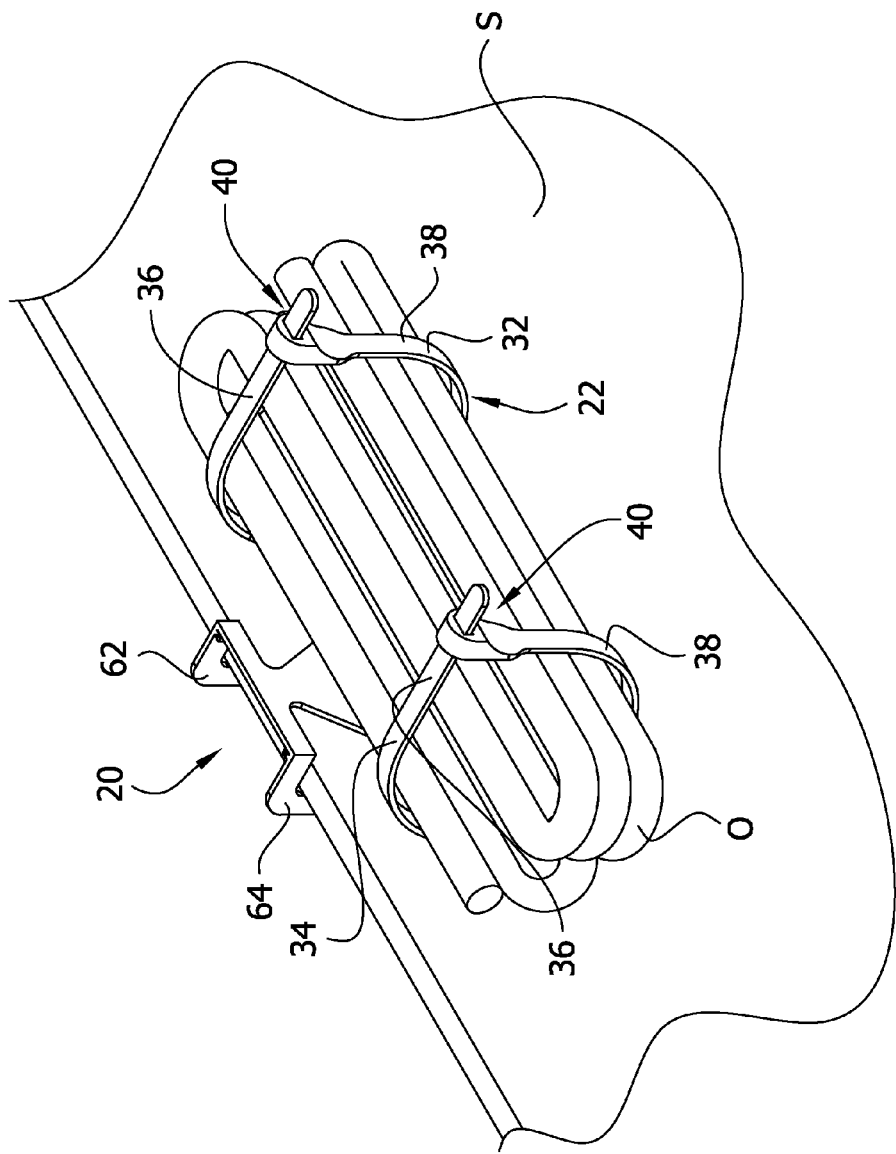
FIG. 17 is a perspective view of the holder of FIG. 1, shown with the loop portion secured around a flexible elongate object and with movable elements of the holder in a second position and positioned on another structure.

As shown in FIG. 17, the first and second end sections 36, 38 of the first and second loop members 32, 34 may be connected in the closed position around a flexible elongate object O. The folded object O can be received into the loop members 32, 34 when the first and second end sections 36, 38 are opened. The first and second end sections 36, 38 of the first and second loop members 32, 34 can then be moved to the closed position, secured around a flexible elongate object O. To remove the flexible elongate object O from the first and second loop members 32, 34, the first and second loop members 32, 34 can be opened. As will be discussed in more detail below, when the loop members 32, 34 are configured in the closed position and secured around a flexible elongate object O in a folded configuration, the holder 20 may support the flexible elongate object in the folded configuration on a structure S. This arrangement of the flexible elongate object O can, for example, hold the flexible elongate object O in a position above a floor surface and, thus, reduce the likelihood that the flexible elongate object O would create a hazard around a patient's bed. Additionally or alternatively, this arrangement of the flexible elongate object O can, for example, facilitate the transport of the flexible elongate object O (e.g., with the movable portion 26 in the first position to form at least a portion of a handle 28 as shown, for example, in FIG. 1).

Returning to FIGS. 1-14, the spine portion 24 includes a neck portion 50, shoulder portions 52, and lateral end portions 54. The lateral end portions 54 extend laterally beneath the neck portion 50 and shoulder portions 52. The neck portion 50 extends upward from the lateral end portions 52, and the shoulder portions 52 extend away from the neck portion (laterally or rearward away from the loop members 32, 34, depending on whether the holder is in the first position (FIGS. 1-7) or the second position (FIGS. 8-14). As used throughout the present disclosure with respect to the holder 20, the terms defining relative locations and positions of structures and components of the holder, including but not limited to the terms "upward," "downward," "left," "right," "top," and "bottom," are meant to provide a point of reference for such components and structures in the orientation shown in the drawings, with the understanding that the respective locations of such components and structures will depend on the orientation of the holder 20 in use. The terms "inner," "outer" and "lateral" are relative locations with respect to the central axis CA of the holder 20.

When the holder 20 is in the first position, the spine portion 24, including neck portion 50, shoulder portions 52, and lateral end portions 54, is a generally planar structure, forming a handle that can be grasped by a user. The first and second loop members 32, 34 are each attached to a respective one of the lateral end portions 54. The first and second end sections 36, 38 are coupled to the spine portion 24 and extend in opposite directions from the spine portion 24. The first end section 36 of each of the first and second loop members 32, 34 extends upward from the spine portion 24, and the second end section 38 of each of the first and second loop members extends downward from the spine member such that the spine portion 24 forms a part of each loop formed by engagement of the first and second loop members 32, 34. In some embodiments, however, the loop member 32, 34 include only one end portion that extends upward or downward from a lateral end portion 54 of the spine portion 24.

The movable portion 26 is coupled to the spine portion 24, and includes first and second movable elements 62, 64. The first and second movable elements 62, 64 extend from a shoulder portion 52 in opposite directions. More specifically, the first movable element 62 and the second movable element 64 extend downward from respective shoulder portions 52 such that each of the first and second movable elements 62, 64 forms a general hook shape with the respective shoulder portion 52.

The center axis CA is parallel to the handle 28 when the movable elements 62, 64 are in the aligned orientation relative to the spine portion 24 (i.e., the first position). The parallel orientation between the center axis CA and the handle 28 can facilitate carrying a flexible elongate object by, for example, orienting the flexible elongate object relative to the user's body such that the flexible elongate object can be carried on the user's side without interfering with the user's ability to walk.

The spine portion 24 and the movable elements 62, 64 lay generally in the same plane, which is parallel the center axis CA. As discussed above, the movable elements 62, 64 also lie in the same plane as the neck portion 50, shoulder portions 52, and lateral end portions 54 of the spine portion 24. When the first and second movable elements 62, 64 are in the first position forming the handle 28, the handle may be used to grasp the holder 20 so that a user may easily carry the holder from place to place. The movable elements 62, 64 are each sized and shaped to receive a finger under the respective element, and the neck portion 52 is sized to be comfortably received between two fingers (not shown) of an individual who is carrying the holder 20. The shoulder portions 54 and movable elements 62, 64 have an ergonomic profile that conforms to the shape of an individual's fingers for securely and comfortably grasping the holder 20 by the handle 28. The orientation of these elements can facilitate grasping of the handle 28 by the user by, for example, facilitating grasping of the handle 28 with the user's wrist in a neutral position in which the user's palm is facing the user's torso. Facilitating grasping of the handle 28 with the user's wrist in the neutral position can, for example, allow a user to carry the holder 20 with a reduced likelihood of injury and/or with greater control over the holder.

As shown in FIGS. 8-14, in the second position, the first and second movable elements 62, 64 and the center axis CA are nonparallel to one another. The movable elements 62, 64 are generally perpendicular to the center axis CA. Each of the movable elements 62, 64 lies in a separate parallel plane that is perpendicular to the plane of the spine portion 24 when the holder 20 is in the second position to form the hook 30. Each of the movable elements 62, 64 may extend in the opposite direction (e.g. backward) from the direction of the loop members 32, 34 (e.g., forward) when the loop members are in the closed position. The opposite orientation of the loop members 32, 34 and the movable elements 62, 64 in the second position can facilitate, for example, loading and unloading a flexible elongate object with respect to the holder 20, while the holder 20 is secured to a frame. Additionally or alternatively, the opposite direction of the loop members 32, 34 and the movable elements 62, 64 in the second position can facilitate, for example, supporting a flexible elongate object in a cantilevered position with respect to a frame.

Figure 18:
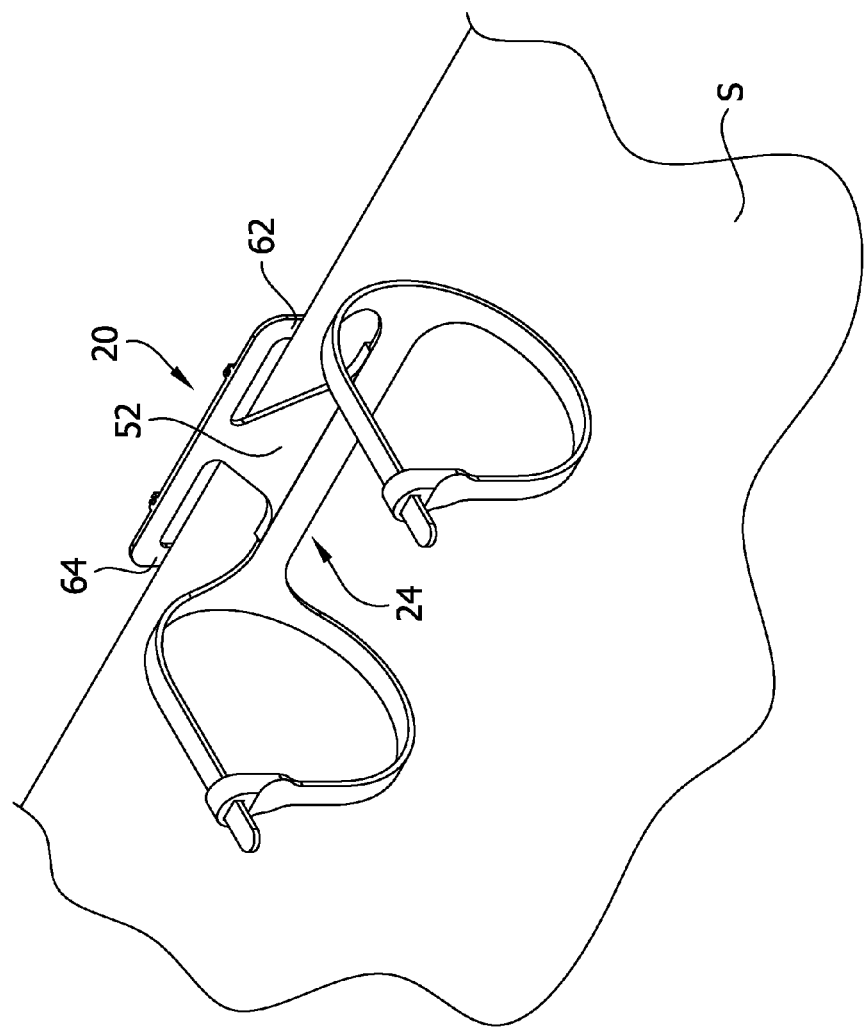
FIG. 18 is a perspective view of the holder of FIG. 1, shown with the movable elements in a first position and positioned on a structure.
Figure 19:
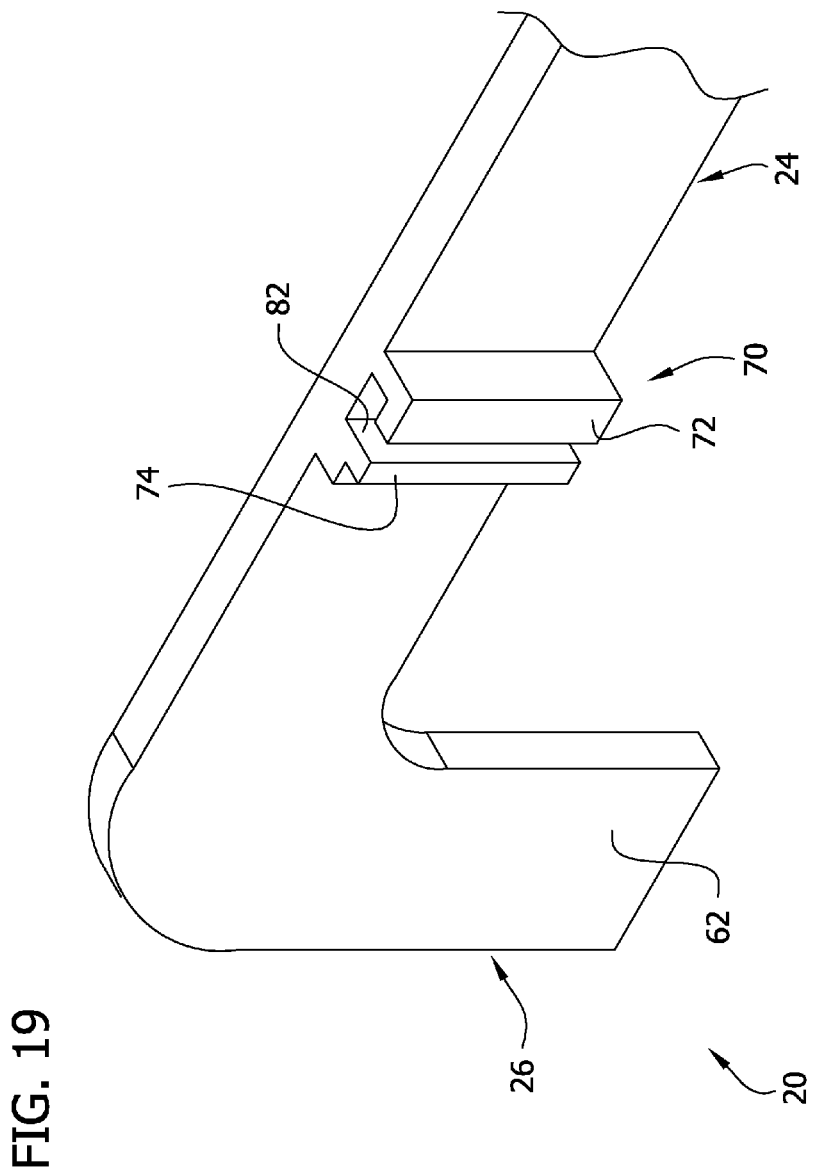
FIG. 19 is an enlarged, fragmentary perspective view of one of the movable elements and a spine portion of the holder of FIG. 1 in the first position and showing a lock in a disengaged configuration.
Figure 20:
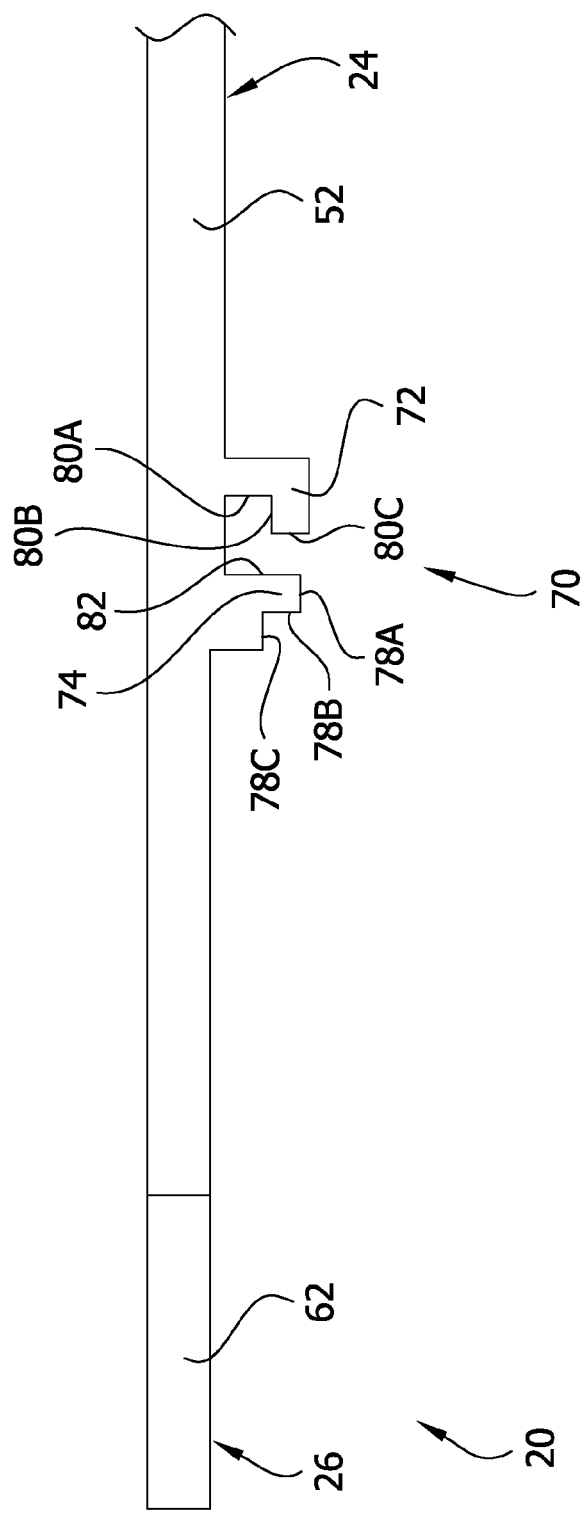
FIG. 20 is an enlarged, fragmentary top elevation view of the movable element and spine portion of the holder of FIG. 1 in the first position and showing the lock in a disengaged configuration.
Figure 21:
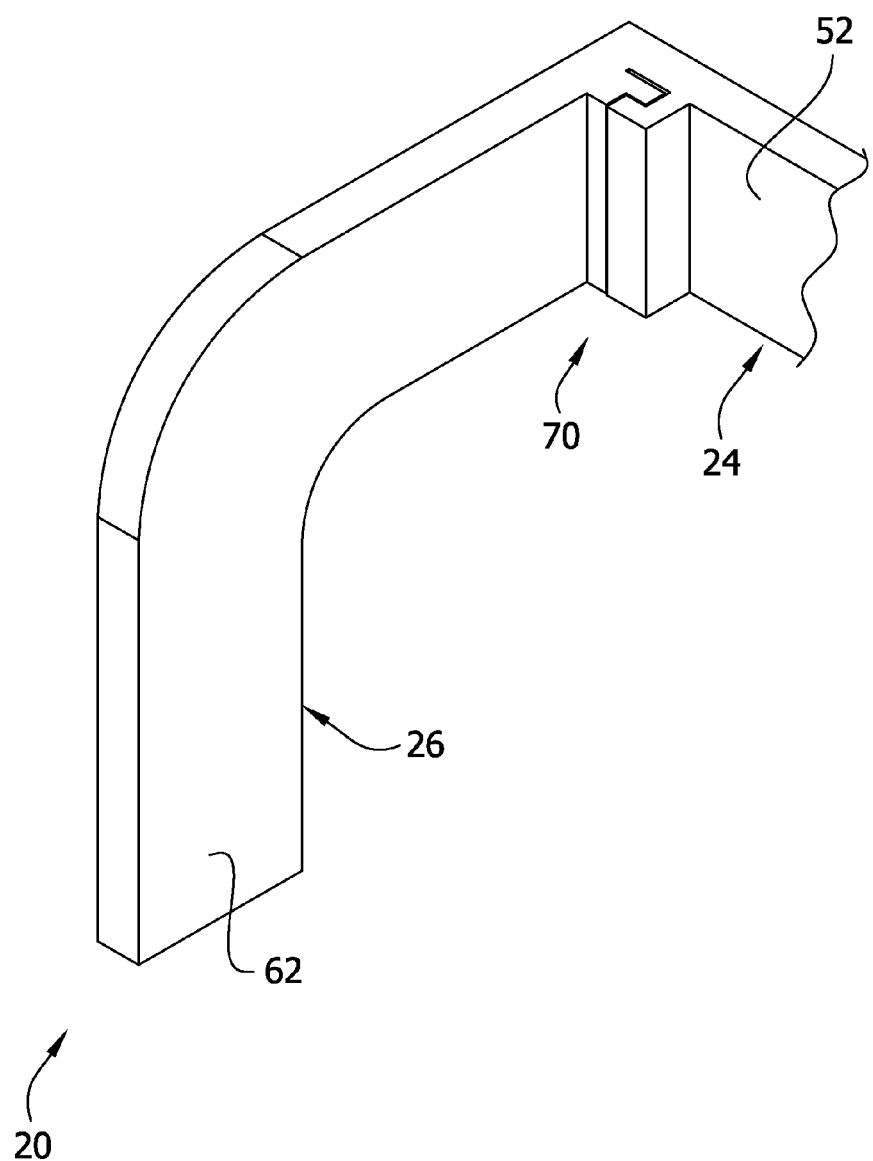
FIG. 21 is an enlarged, fragmentary perspective view of one of the movable elements and the spine portion of the holder of FIG. 1 in the second position and showing the lock in an engaged configuration.
Figure 22:
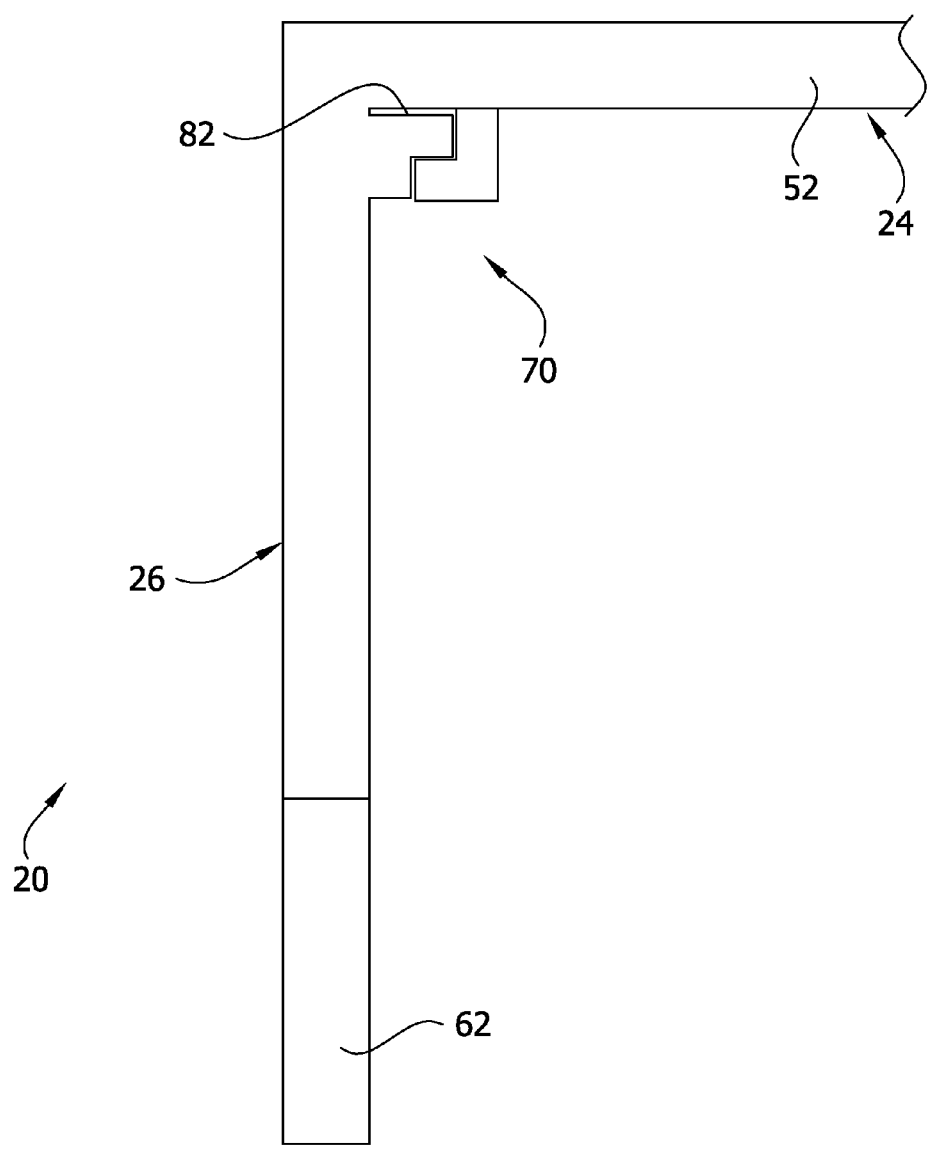
FIG. 22 is an enlarged, fragmentary top elevation view of the movable element and spine portion of the holder of FIG. 1 in the second position and showing the lock in an engaged configuration.

The first and second movable elements 62, 64 are movable between a first position (FIG. 18) and a second position (FIG. 17). A structure S can be positioned between the movable elements 62, 64 and the spine portion 24 in each of the first and second positions. The movable elements 62, 64 are resiliently biased toward the first position, in which the movable elements 62, 64 are coplanar with the spine portion 24. In the first position, the structure S is held between forward facing surfaces of the at least one movable portion 26 and a rearward facing surface of the spine portion 24. In the first position, the movable elements 62, 64 are suitable for attaching the holder 20 to the structure S, provided that the structure S is a thin structure (e.g., a bed sheet) such that the attachment of the holder 20 to the structure S is in the manner of a clip. The movable elements 62, 64 are deflectable slightly from the true first position by the structure S and be urged back toward the true first position, enhancing the grip on the structure S.

In the second position, the first and second movable elements 62, 64 may be spaced from the spine portion 24 to form the hook 30 for receiving the structure S when the structure S is a thick structure (e.g., a bed rail, footboard, headboard, etc.) as compared to the thickness of the types of structures that can be gripped by the holder 20 with the first and second movable elements 62, 64 in the first position. When the movable elements 62, 64 are in the second position and positioned on the structure S to support the holder 20 in a hanging position on the structure, the neck portion 50 and lateral end portions 54 are adjacent a front side of the structure S. The shoulder portions 52 are adjacent a top edge of the structure S, and the free ends of the movable elements 62, 64 are adjacent a back edge and back side of the structure S. An upper edge margin of the structure S may be received under the movable members 62, 64 such that the holder 20 is supported in a self-retaining position (e.g., cantilevered) on the structure S.

Referring now to FIGS. 19-22, the holder 20 includes a lock 70 for releasably locking the movable elements 62, 64 in the second position. Although only the first movable element 62 is shown in FIGS. 19-22, it should be understood that the description of the construction and operation of the first movable element 62 applies equally to the second movable element 64.

The lock 70 includes a channel member 72 and a tab 74 received in the channel member 72 when movable element 62 is in the second position. The channel member 72 may be, for example, an L-shaped, rearward projection. The channel member 72 extends from the rear surface of each of the shoulder portions 52 of the spine portion 24, such that the channel 72 opens laterally to receive the tab 74 in the channel 72. The tab 74 is a stepped structure, sized to be received in the channel 72. The tab 74 includes a plurality of engagement surfaces 78A-C that engage a plurality of opposed engagement surfaces 80A-C of the channel member 72 when the movable element 62 is in the second position. A bracing surface 82 engages the rear surface of the spine portion 24 (the rear surface of a shoulder portion 52) when the movable element 62 is in the second position to prevent the movable element 62 from becoming over-extended.

As the first movable element 62 is moved from the first position to the second position, the tab 74 snaps into the channel member 72 to releasably lock the movable element 62 in the second position. When the tab 74 is received in the channel 72, engaged surfaces 78A-C and 80A-C lock the movable element 62 in the second position. The movable element 62 can be repeatedly transitioned between the first and second positions through, for example, repeated use of the holder 20.

The holder 20 is formed as a one-piece plastic structure. It should be understood, however, that multi-piece assemblies may also be used without departing from the scope of the disclosure. Additionally or alternatively, non-plastic materials may be used. The holder 20 may be formed by a plastic molding process. However, other methods of making the holder 20 for holding a flexible elongate object may additionally or alternatively be used without departing from the scope of the disclosure.

A number of embodiments have been described. Nevertheless, it will be understood that various modifications may be made without departing from the spirit and scope of the disclosure. Accordingly, other embodiments are within the scope of the following claims.

What is claimed is:

1. A holder for holding a flexible elongate object, the holder comprising:
   a loop portion securable around the flexible elongate object with the flexible elongate object in a folded configuration;
   a spine portion coupled to the loop portion;
   at least one movable portion adjustable between a first position, in which the at least one movable portion forms at least a portion of a handle in a substantially coplanar orientation relative to the spine portion such that a single plane, in which the movable portion and the spine lie, intersects both the at least one moveable portion and the spine in the first position, and a second position, in which the at least one movable portion forms at least one hook in a substantially transverse orientation relative to the spine portion, the at least one hook positionable on a structure to support the loop portion in a hanging position on the structure; and
   a lock releasably securable to the at least one movable portion in the second position.

2. The holder of claim 1, wherein the loop portion defines a center axis when secured around the folded configuration of the flexible elongate object, the center axis parallel to portions of the folded flexible elongate object extending through the loop portion, and the center axis of the loop portion is parallel to the handle when the at least one movable portion is in the substantially coplanar orientation relative to the spine portion.

3. The holder of claim 2, wherein, in the second position, the at least one movable portion and the center axis are non-parallel to one another.

4. The holder of claim 3, wherein, in the second position, the at least one movable portion is generally perpendicular to the center axis.

5. The holder of claim 2, wherein the loop portion comprises a first loop member and a second loop member, the first and second loop members axially aligned with one another along the center axis.

6. The holder of claim 5, wherein the first and second loop members are coupled to the spine portion, at opposite ends of the spine portion.

7. The holder of claim 6, wherein the at least one movable portion is connected to the spine portion generally between the first and second loop members.

8. The holder of claim 2, further comprising a vertical plane extending through the center axis, wherein the vertical plane is laterally spaced from said single plane in the first position.

9. The holder of claim 1, wherein the spine portion defines a channel and the lock comprises a tab receivable in the channel when the at least one movable portion is in the second position.

10. The holder of claim 1, wherein the at least one hook, formed by the at least one movable portion in the second position, is adjustable between a first hanging position and a second hanging position, the structure positionable between the at least one movable portion and the spine portion in each of the first and second hanging positions.

11. The holder of claim 10 wherein, in the first hanging position, the movable portion is resiliently biased toward the first position in which the at least one movable portion is substantially coplanar with the spine portion.

12. The holder of claim 11, wherein the lock is releasably securable to the at least one movable portion in the second hanging position.

13. The holder of claim 1, wherein the loop portion includes first and second end sections releasably attachable to one another to secure the loop portion around the flexible elongate object in the folded configuration.

14. The holder of claim 1, wherein the loop portion includes a releasably attachable clasp.

15. The holder of claim 1 wherein the at least one movable portion comprises at least two movable portions, and wherein the spine tapers from the loop portion to a neck portion, the spine including shoulder portions projecting in opposite directions from the neck portion and the two movable portions pivotally connected to respective ones of the shoulder portions for pivoting with respect to the shoulder portions between the first and second positions.

* * * * *